United States Patent
Downey et al.

(10) Patent No.: US 6,190,304 B1
(45) Date of Patent: Feb. 20, 2001

(54) ENHANCED INTRA-AORTIC BALLOON ASSIST DEVICE

(75) Inventors: H. Fred Downey; Xiaoming Bian, both of Fort Worth, TX (US)

(73) Assignee: University of North Texas Health Science Center at Fort Worth, Fort Worth, TX (US)

(*) Notice: Under 35 U.S.C. 154(b), the term of this patent shall be extended for 0 days.

(21) Appl. No.: 09/352,814

(22) Filed: Jul. 13, 1999

(51) Int. Cl.⁷ .................................................. A61M 1/10
(52) U.S. Cl. ..................... 600/18; 604/914; 604/101.05
(58) Field of Search ................... 600/16–18; 604/509, 604/96.01, 97.01, 101.01, 101.05, 103.05, 914, 919; 623/3.1

(56) References Cited

U.S. PATENT DOCUMENTS

| | | | |
|---|---|---|---|
| 3,692,018 | 9/1972 | Goetz et al. | 128/1 R |
| 3,720,200 | 3/1973 | Laird | 128/1 D |
| 4,459,977 | * 7/1984 | Pizon et al. | 600/17 |
| 4,527,549 | 7/1985 | Gabbay | 128/1 D |
| 4,771,765 | 9/1988 | Choy et al. | 600/18 |
| 4,902,273 | 2/1990 | Choy et al. | 600/18 |
| 5,413,549 | * 5/1995 | Leschinsky | 600/18 |
| 5,891,012 | * 4/1999 | Downey et al. | 600/17 |
| 6,090,096 | * 7/2000 | St. Goar et al. | 604/509 |

OTHER PUBLICATIONS

K. H. Scholz et al., "Complications of Intra–Aortic Balloon Counterpulsation", European Heart Journal, 1998, vol. 19, pp. 458–465.

Niccolò Marchionni, MD, et al., "Effective Arterial Elastance and the Hemodynamic Effects of Intraaortic Balloon Counterpulsation in Patients with Coronary Heart Disease", American Heart Journal, May 1998, pp. 855–861.

Jackie Davidson, MS, et al., "Intra–Aortic Balloon Pump: Indications and Complications", Journal of the National Medical Association, vol. 90, No. 3, pp. 137–140.

David F. Torchiana, MD, et al., "Intraaortic Balloon Pumping For Cardiac Support: Trends In Practice And Outcome, 1968 to 1995", The Journal of Thoracic and Cardiovascular Surgery, vol. 113, No. 4, pp. 758–769.

Ch. E. Charitos, et al., "The Efficacy of the High Volume Counterpulsation Technique at Very Low Levels of Aortic Pressure", The Journal of Cardiovasular Surgery, vol. 39, No. 5, pp. 625–632.

* cited by examiner

Primary Examiner—Kennedy Schaetzle
(74) Attorney, Agent, or Firm—Charles D. Gunter, Jr.; Kevin M. Faulkner (57) ABSTRACT

The present invention is an intra-aortic circulatory enhancing apparatus for use in human patients to improve blood flow to other arteries continuous with the aorta of the patient. The apparatus comprises an internal inflation means located within the aorta of the patient and an external inflation means located outside of the patient. The internal inflation means can be an internal balloon coupled to a hollow extent which is operatively coupled to a blood communication means. The blood communication means can be a first hollow catheter tube in one embodiment. The external inflation means can be an external balloon coupled to a hollow extent running through the center of the balloon and continuous with a second hollow catheter tube. The blood communication means is coupled to the internal and external inflation means, allowing blood within the aorta to communicate with the secondary inflation means.

38 Claims, 6 Drawing Sheets

ENHANCED INTRA-AORTIC BALLOON ASSIST DEVICE

BACKGROUND OF THE INVENTION

1. Field of the Invention

The present invention relates to intra-aortic balloon pumps ("IABP") that act as a left ventricular assist device ("LVAD"). More particularly, the present invention relates to a cooperatively acting dual balloon system wherein one balloon is located inside the aorta and a second balloon is located outside the body, a hollow catheter allowing for blood communication between the second balloon and the aorta.

2. Description of the Prior Art

The intra-aortic balloon pump ("IABP") is by far the most commonly utilized left ventricular assist device ("LVAD"). This device is used when the patient's cardiac output is not sufficient to maintain an adequate blood pressure for supplying the patient's organs with arterial blood.

The IABP consists of an inflatable balloon attached to a catheter, which is advanced through the patient's femoral artery and into the descending aorta. Inflation and deflation of the balloon is accomplished by an external control unit synchronized with the heart beat. This unit rapidly inflates the balloon during the diastolic or resting phase of the heart cycle, and thus elevates diastolic aortic blood pressure and improves blood flow to the heart, the brain and other tissues. The balloon is rapidly deflated as the heart contracts. This reduces the aortic blood pressure that the heart must overcome to eject blood from the left ventricle. Thus, the IABP is a LVAD that also augments diastolic aortic blood pressure.

However, present IABP devices cannot sustain the circulation if the heart is severely diseased or injured, since ventricular ejection must be sufficient to keep the mean aortic blood pressure above approximately 60 mmHg. When the aortic pressure falls below this value, there is insufficient blood to fill the space around the balloon when it is deflated. In that case the wall of the aorta collapses around the deflated balloon of prior art devices, and the IABP becomes ineffective. Thus, present IABP devices can be used only in less severe cases of left ventricular failure.

The present invention is directed towards improving the usefulness of IABP devices by enhancing the use of a single balloon in the descending aorta with a second, external balloon located outside the body and in direct communication with the blood within the aorta through a hollow catheter tube connecting both balloons. Although several IABP devices have used multiple balloons to enhance circulation, none use an external balloon working cooperatively with the internal balloon. Gabbay (U.S. Pat. No. 4,527,549) discloses the use of a balloon within the ascending aorta and multiple smaller balloons within the aortic arch and descending aorta. Given the difficulty in positioning a balloon within the ascending aorta with a catheter coming up from the descending aorta, the Gabbay device is cumbersome and difficult to operate. More importantly, the Gabbay device has the disadvantage of being positioned in the ascending aorta in order to function, thus increasing the chance of producing emboli that can cause problems such as stroke. Choy et al. (U.S. Pat. No. 4,902,273) discloses a dual balloon device, but which operates by a completely different mode. In the Choy et al. device, one balloon enters the left ventricle of the heart and another balloon enters the right ventricle of the heart. In a diseased heart, which may already be dilated, this would excessively expand the ventricle and may cause rupture or other permanent damage. Positioning the balloons in that invention is also cumbersome, making the device impractical for many applications.

Thus, what is needed is a IABP that has greater pumping capacity, that is simple to use and capable of rapid insertion and operation in an emergency situation, and that is capable of elevating blood pressure within the ascending aorta even if the descending aorta should collapse around the internal pumping balloon. The present invention is directed towards such a device.

SUMMARY OF THE INVENTION

One object of the present invention is to provide a means and method for enhancing heart function when the blood pressure within the aorta is insufficient to prevent the collapse of the descending aorta around the intra-aortic balloon.

Another object of the present invention is to enhance the blood flow to the heart, brain, and other tissues under the conditions of poor heart function.

Another object of the present invention is to provide a means for enhancing the pumping and sucking effect of an IABP within the aorta by using a simple, unitary device that is self contained and easy to use.

Yet another object of the present invention is to provide a means of enhancing the perfusion of other arteries such as the renal arteries and the aortic arch arteries.

Yet another object of the present invention is to provide a dual balloon IABP that acts cooperatively through a continuous unit, the size of which can be varied to adapt to the size of the patient or the desired amount of pumping.

These objects are achieved in the present invention by an intra-aortic circulatory enhancing apparatus for use in human patients to improve blood flow to other arteries continuous with the aorta of the patient. The apparatus comprises an internal inflation means located within the aorta of the patient and an external inflation means located outside of the patient. The internal inflation means can be an internal balloon coupled to a hollow extent which is operatively coupled to a blood communication means. The blood communication means can be a first hollow catheter tube in one embodiment. The external inflation means can be an external balloon coupled to a hollow extent running through the center of the balloon and continuous with a second hollow catheter tube. The blood communication means is coupled to the internal and external inflation means, allowing blood within the aorta to communicate with the secondary inflation means. Further, a pressurization means for pressurizing and depressurizing the internal and external balloons is provided. The pressurization control means is a lumen in one embodiment of the invention, the lumen associated with the balloons and extending from the balloons to be coupled to an external control unit. When operating, the balloons pump simultaneously, then draw or suck blood simultaneously, thus helping to generate blood flow. The balloons pressurize and depressurize simultaneously, thus acting cooperatively to enhance the blood-pumping action of a diseased human heart and enhance blood flow to the heart, brain, and other tissues.

Additional objects, features and advantages will be apparent in the written description which follows.

DETAILED DESCRIPTION OF THE INVENTION

Appartus

One embodiment of the present invention utilizes an internal inflation means in the form of an inflatable balloon in the descending aorta similar to that of present IABP devices, but has additional cooperative pumping capacity. This additional capacity is provided by an external inflation means, in the present embodiment an inflatable balloon, in a chamber outside the body. The internal and external inflation means are not limited to being in the form of a balloon, but can take other forms consistent with the function of pumping and sucking blood to and from the aorta of the patient under conditions of poor heart function.

Figure 1:
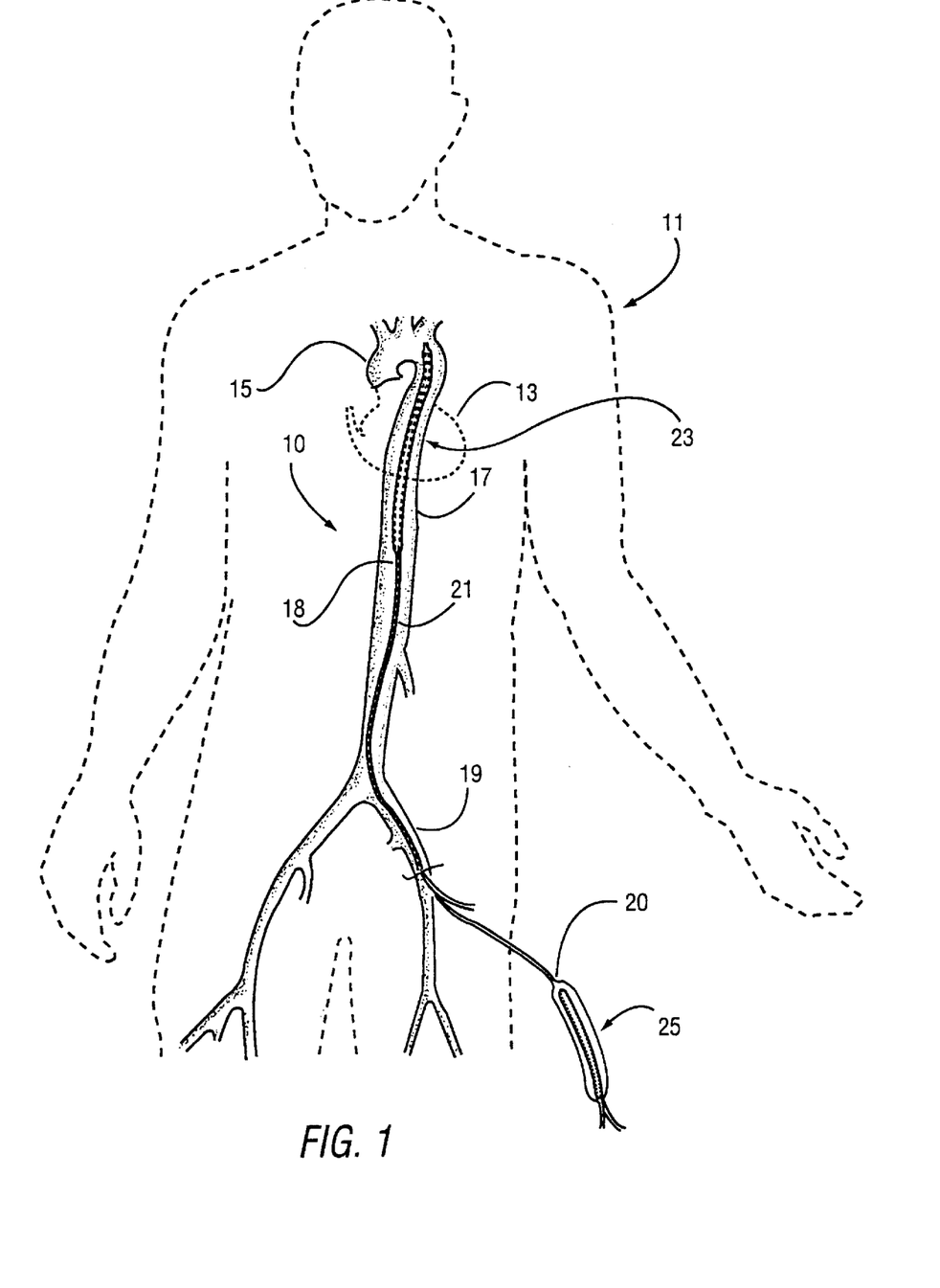
FIG. 1 is a fanciful view of portions of the human body and the apparatus of the invention inserted therein.
Figure 2:
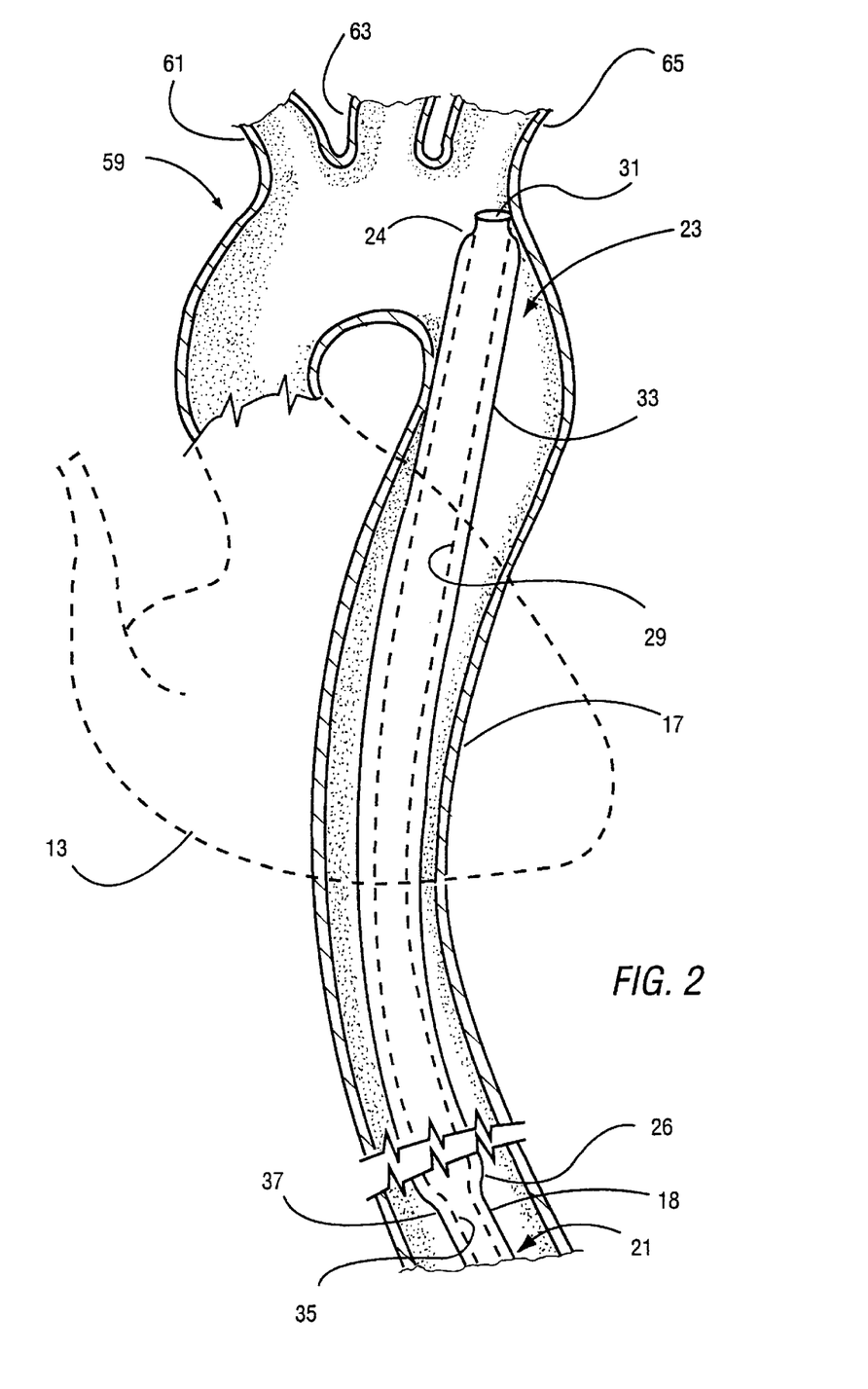
FIG. 2 is an exploded, detailed view of the internal inflation means of the invention.

The present invention is first described with reference to FIG. 1, wherein the apparatus 10 is a continuous unit that is reversibly implanted into patient 11 having heart 13, ascending aorta 15, and descending aorta 17. Within the patient is the internal inflation means 23, and outside the patient is external inflation means 25. The inflation means in the present embodiment are balloons coupled to hollow extents running through the center of the balloons, the balloons being made from a flexible and nonthrombogenic material. The hollow extents are made from rigid and flexible material, typically the same material used for the first hollow catheter tube 35 (FIG. 2). Although the hollow extent is described as running through the center of the internal balloon, the balloon and extent can also be placed in other configurations consistent with the invention. The two inflation means 23 and 25 communicate through the tube assembly 21 having a distal end 18 and proximal housing end 20.

Figure 3:
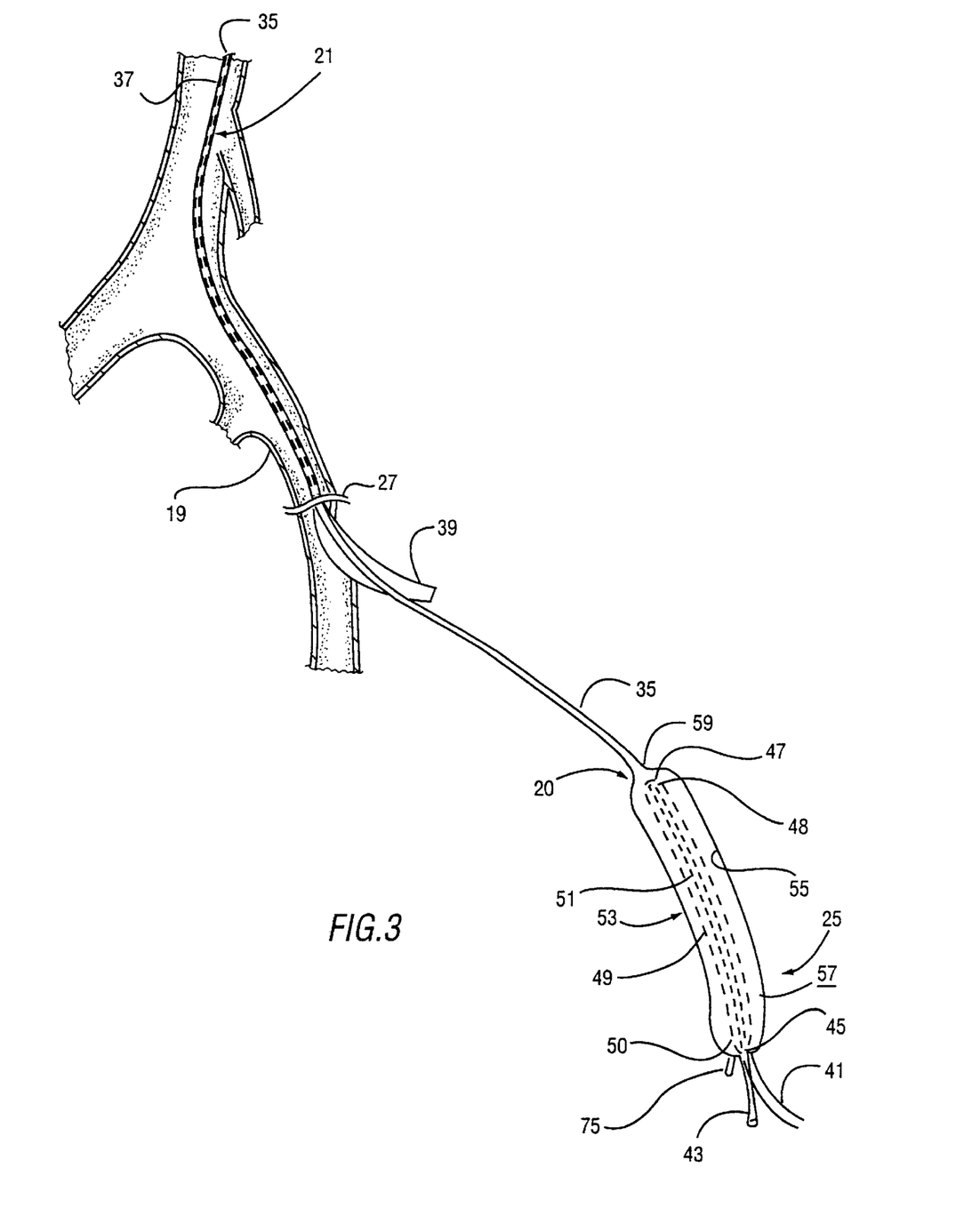
FIG. 3 is an exploded, detailed view of the external inflation means of the invention.
Figure 4:
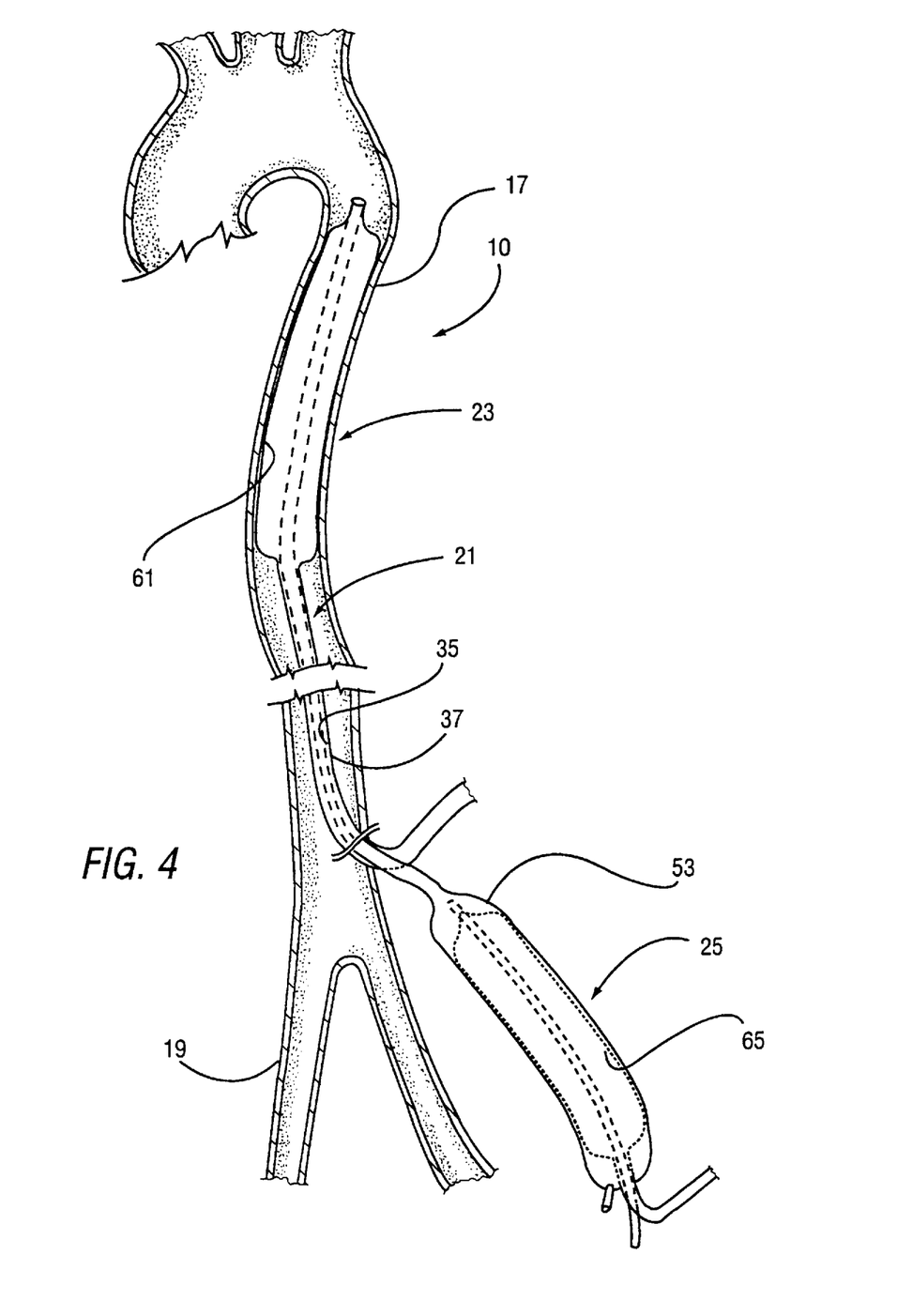
FIG. 4 is an exploded, cutaway view of the apparatus in the patient in the pressurized position.

The further description of the apparatus is best understood with reference to the placement in the patient's body. A surgical incision 27 is made in the patient 11 such that the internal inflation means 23 can be inserted first into the femoral artery 19, and up into the descending aorta 17. The internal inflation means 23 is pushed up into the aorta by applying force upon the tube assembly 21 which is rigid and flexible. Referring to FIGS. 2–4 the tube assembly is further described. The tube assembly 21 comprising first hollow catheter tube 35 and first lumen 37. The first hollow catheter tube 35 serves as a blood communication means in the present embodiment although other tube or channel creating structures are appropriate for the passage of blood. The first hollow catheter tube 35 is continuous with the hollow extent 29, thus allowing blood to flow through to opening 31 and in communication with the aorta of the patient. The first hollow catheter tube 35 is made from a rigid material that is formed into a tube having a hollow interior continuous with its length. The hollow catheter tube is made from a rigid yet flexible material that is non-thrombogenic.

A pressurization means is provided to pressurize the internal inflation means. The pressurization means can be any continuous tube, lumen, or tube-like structure that starts from the proximal end 26 of balloon 33 and extends a length along the first hollow catheter to allow pressurizing gas to enter and exit the internal balloon 33. The internal balloon 33 in FIG. 2 is shown in a partially pressurized state in going to the pressurized state as shown in FIG. 4. In the present embodiment shown in FIG. 2, the pressurization means is first lumen 37. The lumen is continuous with the first hollow catheter tube 35, and operatively coupled to the internal balloon 33.

The first hollow catheter tube 35 extends into the internal balloon through extent 29, the extent terminating at opening 31. This opening allows blood within the aorta to communicate through extent 29 into the length of the first hollow catheter tube 35, and ultimately to the external inflation means described further infra. The internal balloon has a distal end 24 and a proximal end 26, the distal end typically placed in the descending aorta 17 near the aortic arch 59.

Tube assembly 21 couples the internal and external inflation means and allows blood communication from the aorta to the external inflation means 25. External inflation means 25 is described with reference to FIG. 3. Extending from the proximal end 26 of internal inflation means 23, the tube assembly 21 extends through the descending aorta and into the femoral artery, exiting the patient 11 at incision 27, coupling with the external inflation means 25. The first lumen 37 extends away from the first hollow catheter 35 to form first pressurization tube 39.

First hollow catheter tube 35 extends outside the patient to form catheter housing 53, the housing having an internal wall 55 that forms pumping chamber 57. The catheter tube 35 can extend most any length from the internal inflation means 23 to the external inflation means 25, the length from distal end 18 to proximal end 20 depending on the size of the patient. Thus, the apparatus 10 can be made to various sizes to be used on patients of various sizes, from small children to larger adults.

Within the chamber 57 is the external pumping balloon 49, the external balloon being coupled to a second hollow catheter tube 43. The balloon 49 is shown in FIG. 3 in a partially pressurized state in going to the fully pressurized state of FIG. 4. Extending through the center of the balloon is extent 51, which forms a sensor opening 47. The extent 51 is continuous with the catheter tube 43, thus allowing a pressure sensor to be coupled to the catheter tube 43 for sensing the blood pressure within chamber 57. The sensor opening 47 is located at the distal end 48 of external balloon 49, the proximal end 50 of balloon 49 narrowing to second lumen 45. The second lumen 45 then exits the housing 53 to form pressurization tube 41. The internal walls 55 are of a diameter such as to allow the external balloon 49 to pressurize until it fills the volume of chamber 57.

A pressurization means is provided for inflating and deflating (pressurizing and depressurizing) the balloons of the invention. The pressurization means is first pressurization tube 39 and second pressurization tube 41 extending a length to be coupled to an external control unit (not shown), the unit being designed to supply a gas such as helium to the balloons of the invention. The gas is pressurized to inflate the balloons into a pumping position, and depressurized to deflate the balloons into a sucking position. Thus, blood is pumped and drawn to facilitate the heart's function. Second hollow catheter tube 43 can be used to inject substances into the patient and to couple to a pressure sensing device located external to the patient. The pressure sensor would measure the change in pressure within chamber 57 during systole and diastole of the left ventricle.

The pumping action of the balloons is controlled by an electrocardiogram, wherein the detected depolarization of the heart muscles (contraction) triggers the external control unit to depressurize and deflate those balloons. The external control unit is programmed by the user to automatically trigger the inflation of the balloons when the heart muscle relaxes.

Operation

The mode of operation of the apparatus is now described. Once the internal inflation means 23 is in position within the aorta, blood is allowed to purge into the first catheter 35 through opening 31. The blood is communicated down the length of the catheter 35 into chamber opening 59 and filling chamber 57. As blood enters and fills chamber 57, air within chamber 57 escapes through one-way air valve 75. The air valve 75 is coupled to the housing 53, preferably close to the position of the pressurization tube 41 on housing 53. A one-way air valve is common and its design and use is understood by those skilled in the art.

During systole, the left ventricle contracts and expels blood into the aorta. At this stage, the external control unit is triggered by the electrocardiogram to depressurize the internal balloon 33 and external balloon 49, thus deflating these balloons. The deflated balloons increase the volume within the aorta 17 and chamber 57. This has the effect of drawing or sucking blood into the descending aorta surrounding the internal inflation means 23 and into the opening 31 and down to chamber opening 59, thus filling the volume of chamber 57.

The balloons of the invention are next pressurized (inflated) by the external control unit, the timing set after a preselected time period following deflation as described supra. Gas flows into lumens 39 and 41 and into external balloon 49 and internal balloon 33, simultaneously pressurizing both balloons. When balloon 33 is pressurized and thus inflated, the volume within the aorta that surrounds the balloon is filled with the balloon material, thus decreasing the volume and forcing blood around the balloon 33 either towards the aortic arch or towards the distal aorta. When balloon 49 is pressurized, the space within chamber 57 is filled with the balloon material. This pushes blood that is within the chamber 57 out chamber opening 59 and into the first hollow catheter tube 35, up to opening 31 and out into the aorta.

FIG. 4 shows the pressurized position of the apparatus 10. The internal balloon is in the fully pressurized (inflated) state 61, while the external balloon is in the fully pressurized (inflated) state 63. As can be seen in FIG. 4, the space surrounding the internal and external balloons is filled by the balloons in the pressurized state, thus decreasing the volume within the aorta 17 and catheter housing 53, respectively. This forces blood away from the balloons to create the pumping action.

The level of pressurization of the internal and external balloons can be controlled by the pressurization means coupled to the external control unit. The degree of inflation can also be controlled by the operator wherein the external control means is set to deliver/withdraw a predetermined amount of gas to and from the balloons. This allows for varying volumes of blood to be delivered through the hollow catheter tube 21 to the aorta of the patient. Also, the external balloon can be independently controlled to allow for various volumes of blood to be delivered to the aorta. Specifically, the external control means can be set by the user to inflate the balloon 49 at a certain level, thus filling chamber 57 to varying degrees. Thus, if the balloon 49 is only partially inflated at its most pressurized state, then chamber 57 will only be partially filled by the balloon, thus delivering a lower volume of blood than could be delivered if the balloon 49 were inflated to its maximum level to fill the chamber 57 completely. This offers the advantage of delivering varying amounts of blood, depending on the size of the patient and/or nature of the heart's condition.

The external control unit rapidly inflates the balloons during the diastolic or resting phase of the heart cycle, and thus elevates diastolic aortic blood pressure and improves blood flow to the heart, brain, and other tissues. The balloons of the invention are rapidly deflated as the heart contracts, thus producing a sucking effect that draws blood from the left ventricle and the ascending aorta. This reduces the aortic blood pressure that the heart must overcome to eject blood from the left ventricle. Thus, the apparatus 10 of the present invention is a LVAD that also augments diastolic aortic blood pressure.

Figure 5:
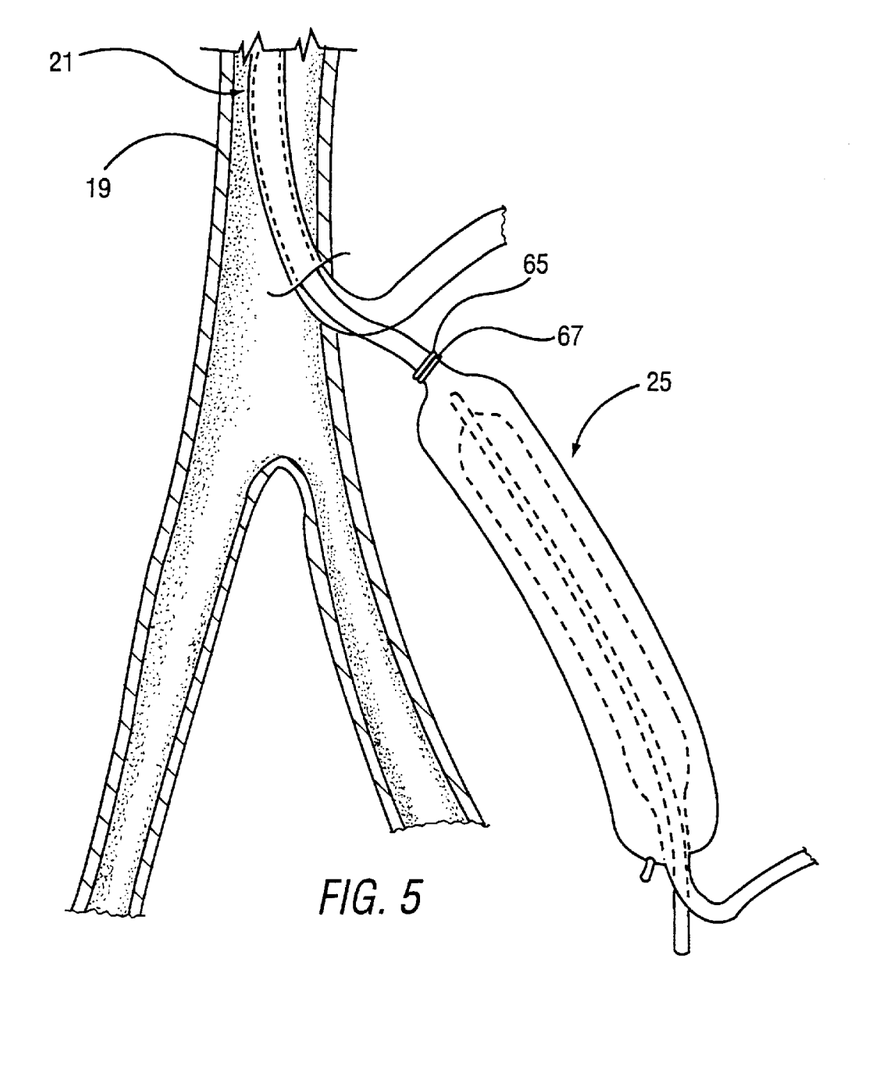
FIG. 5 is an exploded view of the coupling means of the invention.

The pumping and sucking action of the apparatus 10 of the present invention supplies blood to other arteries such as the brachiocephalic trunk 61, left common carotid artery 63, left subclavian artery 65, and renal arteries. Further, the apparatus can be tailored to fit the individual patient. The apparatus can be made from two parts that can be separated and changed out to allow different sized internal inflation means to be coupled to different sized external inflation means. This is described with reference to FIG. 5, wherein a coupling means comprising two mating couplers. A coupler 65 is attached to one end of the tube assembly 21 associated with the internal inflation means 23, and the coupler 67 is attached to an end section of the tube assembly 21 associated with the external inflation means 25. The couplers 65 and 67 can be female and male threaded joints, pressure sensitive joints, or other joints wherein the hollow catheter tube 35 endings make intimate contact with one another so that a firm seal is made for pressurized blood within the catheter to flow uninterrupted.

The size of the internal pumping balloon can be varied depending on the patient size, while the external balloon size can be varied by taking into account such variables as the desired volume defined by chamber 57, thus either increasing or decreasing the volume of blood delivered to the patient. The size of the internal pumping balloon can be independently chosen to fit various sized external pumping balloons, a means being provided to change out one sized internal balloon with another for a given external balloon, and vice versa.

Specifically, the diameter of the tube assembly 21 can be made in many sizes to allow the medical practitioner that is treating the patient to choose from a variety of sizes to fit the size of the patient. The outside diameter of the tube assembly 21 is similar to the inner diameter of the patient's femoral artery 19. This relatively large diameter allows rapid and efficient movement of blood between the ascending aorta 15 and the external inflation means 25. The external balloon 49 located in the pumping chamber 57 will be deflated and inflated at the same time as the internal balloon, and both balloons will be operated by an external control unit, similar to that of the present IABP. Thus, deflation of the balloon in the pumping chamber will further lower aortic pressure during left ventricular ejection. Should the aortic systolic pressure be so low that the walls of the aorta contract around the internal balloon, deflation of the balloon in the pumping chamber will still withdraw blood from the ascending aorta, since the walls of the pumping chamber are rigid. Further, the tube assembly 21 is rigid and made wide enough so that a passage for blood remains even if the aorta collapses around the internal inflation means 23. Operation of the external inflation means 25 will pump and suck blood into and out of the aorta even if the pumping action of the internal inflation means 23 is ineffective. Thus, the external inflation means 25 will augment, or in severe conditions, supplant the action of the internal inflation means.

Figure 6:
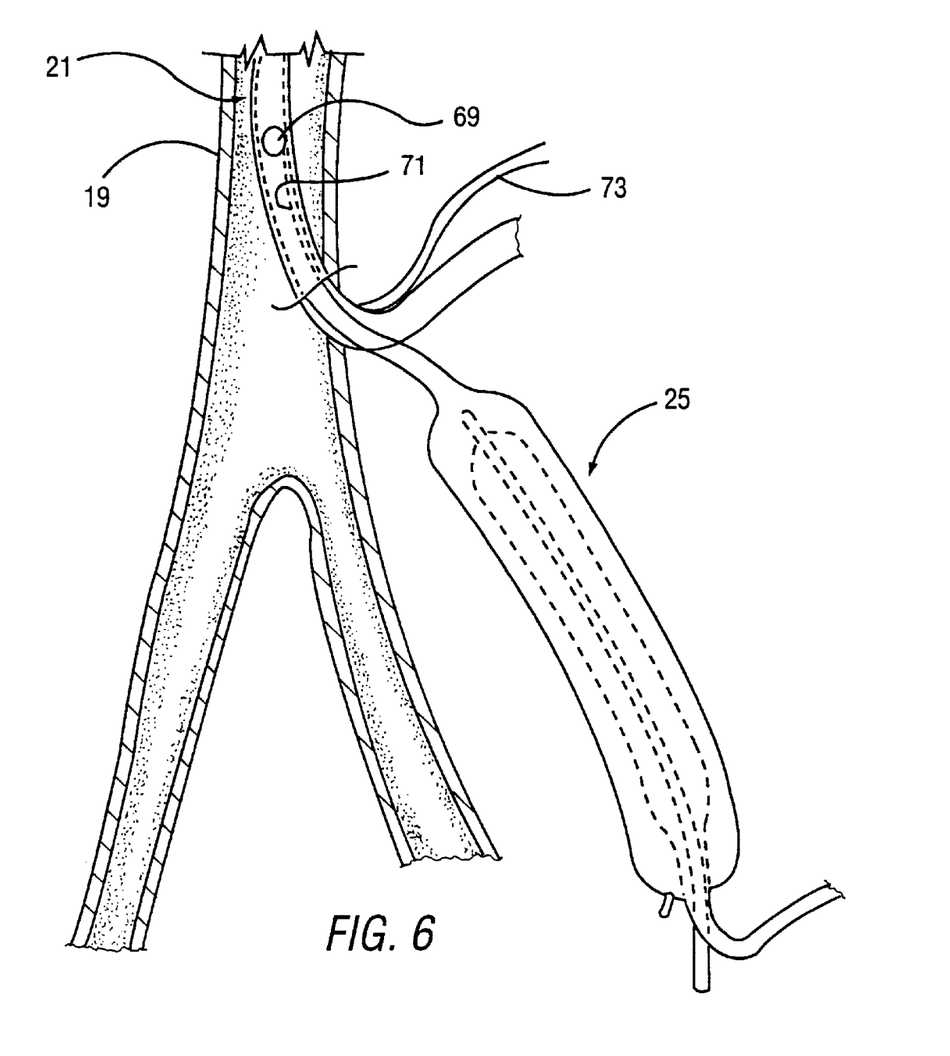
FIG. 6 is an exploded view of the perfusion eyelet of the invention.

In another embodiment of the present invention shown in FIG. 6, the tube assembly 21 has a perfusion eyelet 69. The perfusion eyelet is an opening into the hollow catheter tube 35 that allows communication of blood between the tube 35 and the surroundings within the aorta. The perfusion eyelet 69 has an open and a closed position, the opening and closing being controlled by a donut-shaped balloon surrounding the opening of the eyelet. The eyelet operates much like the iris of an eye, wherein the donut-shaped balloon is fabricated to allow for the closing of the opening upon inflation without obstructing the lumen of the tube assembly 21.

The donut-shaped balloon can be pressurized to close the opening, thus not allowing blood communication between the aorta and first hollow catheter tube 35, and depressurized to hold the eyelet open, thus allowing blood communication. A separate lumen 71 and pressurization tube 73 continuous therewith is provided for inflating and deflating the donut-shaped balloon. The eyelet would preferably be located at a region of the tube assembly 21 within the descending aorta once the apparatus is in place within patient 11. The position of the eyelet 69 in FIG. 6 is for illustration only and is not intended to limit its actual position along tube assembly 21. The perfusion eyelet would allow perfusion of the kidneys through the left and right renal arteries even if the descending aorta collapses around the internal balloon. During deflation of balloon 49, the eyelet would also facilitate the entry of blood into chamber 57 by allowing blood from the descending aorta to enter the eyelet and travel down the catheter tube 35 to fill chamber 57.

One advantage of the present invention lies in the ability of the apparatus to pump and suck blood within the descending aorta even when the aorta collapses. The tube assembly is rigid yet flexible, and of a diameter such that if the aorta collapses around the internal balloon, it does so only to the extent that the tube assembly will allow. The tube assembly, having the hollow catheter tube and coupled to the hollow extents, creates a channel through which blood can communicate with the external balloon. Thus, the external balloon can pump and suck blood if the internal balloon is ineffectual.

Another advantage lies in the external balloon itself. The arrangement of the external balloon with the internal balloon allows an enhanced pumping and sucking action when both balloons are functioning. This further enhances circulation of blood to the ascending aorta and other aortic arteries.

Yet another advantage of the invention is its simplicity. The apparatus is a singular, unitary design that essentially resides in one housing that can be inserted into a patient's femoral artery and up to the descending aorta, a common medical procedure. This will allow the apparatus to be used in emergency situations, and more easily in all situations. The apparatus can be made from two parts that can be separated and changed out to allow different sized internal inflation means to be coupled to different sized external inflation means.

Yet another advantage of the present invention is the ability to optionally eject blood into the descending aorta to improve renal blood flow.

Yet another advantage of the present invention is the ability to vary the pumping capacity of the apparatus by varying the volume of chamber 57 and/or controlling the level of inflation of external balloon 49.

Yet another advantage of the apparatus is that the placement of the external balloon. The external balloon is placed external from the patient yet in communication with the blood. This allows for more space within the aorta for the internal balloon and fewer internally placed foreign objects, thus reducing the chances of a thrombogenic reaction.

While the invention has been shown in only one of its forms, it is not thus limited but is susceptible to various changes and modifications without departing from the spirit thereof

What is claimed is:

1. An intra-aortic circulatory enhancing apparatus for use in human patients to improve blood flow through the aorta and to other arteries continuous with the aorta of the patient, the apparatus comprising:

an internal inflation means that is positionable within the aorta of the patient;

an external inflation means that is positionable outside of the patient;

a blood communication means for coupling the internal and external inflation means, allowing blood within the aorta to communicate with the external inflation means; and further comprising a pressurization means for pressurizing and depressurizing the internal and external inflation means, the internal and external inflation means alternately pumping and sucking blood to and from the other arteries, respectively, when the internal inflation means is positioned within the aorta of a patient, thus acting cooperatively to enhance the blood-pumping action of a diseased human heart.

2. The apparatus of claim 1, wherein the internal inflation means is an internal balloon having a pressurized position and depressurized position.

3. The apparatus of claim 1, wherein the external inflation means is an external balloon having a pressurized position and a depressurized position.

4. The apparatus of claim 1, wherein the pressurization means comprises a first lumen operatively coupled to the internal balloon and a second lumen operatively coupled to the external balloon, the first and second lumens being coupled to a external control unit.

5. The apparatus of claim 1, wherein the blood communication means is a first hollow catheter tube having a distal end located within the aorta of the patient and a proximal housing end located outside the patient.

6. The apparatus of claim 5, wherein the external balloon is located within the proximal housing end.

7. The apparatus of claim 1, wherein the external inflation means is coupled to a second hollow catheter tube.

8. The apparatus of claim 7, wherein the second hollow catheter tube can be coupled to a pressure sensing device.

9. The apparatus of claim 7, wherein the second hollow catheter tube can be used to inject substances into the human.

10. The apparatus of claim 5, wherein the first hollow catheter tube extends a length such that the catheter extends at least the length starting from the heart of the human and ending at the femoral artery of the human.

11. The apparatus of claim 1, wherein a perfusion eyelet having an open and a closed position is associated with the first hollow catheter tube.

12. The apparatus of claim 11, wherein the perfusion eyelet is closed by pressurizing a circular balloon located circumferentially at the eyelet and opened by depressurizing the circular balloon.

13. The apparatus of claim 12, wherein a eyelet lumen is coupled to the circular balloon to independently control the pressurizing of the circular balloon.

14. The apparatus of claim 5, wherein the hollow catheter tube has an opening that allows blood to flow into the first hollow catheter tube and in communication with the external balloon when the catheter tube is located inside of a human aorta.

15. An intra-aortic circulatory enhancing apparatus for use in a human patient to improve the function of a weak or diseased heart, the apparatus comprising:
    an internal balloon having a proximal end and a distal end, the internal balloon being coupled to a first hollow catheter tube;
    the hollow catheter tube extending a length from the distal end of the internal balloon to form a balloon housing;
    an external balloon coupled to a second hollow catheter tube, the external balloon residing within the balloon housing;
    a pressurization means for pressurizing the internal and external balloons; and
    wherein the internal balloon is adopted for placement within an aorta of the human and the external balloon is located outside of the patient.

16. An intra-aortic circulatory enhancing apparatus for use in humans to improve the function of a weak or diseased heart, the apparatus comprising:
    an external balloon located within a catheter housing having a proximal end and a distal end, the catheter housing distal end extending to form a hollow catheter tube to which an internal balloon is coupled, the hollow catheter tube having an opening that allows blood to flow into and out of the catheter;
    the internal balloon and hollow catheter tube adopted for placement within a descending aorta of a human and surrounded by blood such that blood flows into the opening of the hollow catheter to the catheter housing and surrounding the external balloon;
    a pressurization means coupled to the internal and external balloons to pressurize the balloons; and
    wherein the external balloon can be pressurized to push blood out of the catheter housing and through the hollow catheter into the aorta of a patient, and wherein the internal balloon can be simultaneously pressurized to push blood towards the aortic arch and the lower extremities.

17. The apparatus of claim 16, wherein the pressurization means comprises a first lumen operatively coupled to the internal balloon and a second lumen operatively coupled to the external balloon, the first and second lumens being coupled to a external control unit.

18. The apparatus of claim 16, further providing a second hollow catheter tube that extends the longitudinal length of the external balloon and is coupled to the external balloon.

19. The apparatus of claim 17, wherein the second hollow catheter tube can be coupled to a pressure sensing device.

20. The apparatus of claim 16, wherein the second hollow catheter tube can be used to inject substances into the human.

21. The apparatus of claim 16, wherein the hollow catheter tube extends a length such that the catheter exits the human at the femoral artery.

22. The apparatus of claim 16, wherein a perfusion eyelet having an open and a closed position is associated with the first hollow catheter tube.

23. The apparatus of claim 22, wherein the perfusion eyelet is opened by pressurizing a circular balloon located circumferentially at the eyelet.

24. The apparatus of claim 23, wherein a eyelet lumen is coupled to the circular balloon to independently control the pressurizing of the circular balloon.

25. The apparatus of claim 16, wherein a gas is used to pressurize the internal and external balloons.

26. The apparatus of claim 16, wherein the balloons and the hollow catheter tube of the device are fitted to the size of the patient using detachable parts.

27. A method of assisting the function of a weak or diseased heart in order to supply blood to the upper and lower extremities of a human, the method comprising:
    providing an internal balloon having a proximal end and a distal end, the internal balloon being coupled longitudinally to a first hollow catheter tube, the hollow catheter tube having an opening which is at the distal end of the internal balloon, the hollow catheter tube extending a length proximally from the internal balloon to form a balloon housing;
    further providing an external balloon coupled longitudinally to a second hollow catheter tube, the external balloon residing within the balloon housing;
    placing the internal balloon within the descending aorta of the human such that the hollow catheter tube opening is facing the aortic arch and the external balloon housing is located outside of the human;
    allowing blood to enter the catheter opening such that blood flows into the external balloon housing and surrounds the external balloon while blood also flows around and surrounds the internal balloon;
    alternately pressurizing and depressurizing the internal balloon while simultaneously pressurizing and depressurizing the external balloon, thus forcing the blood surrounding the external balloon into the hollow catheter tube and out the catheter opening into the aortic arch and forcing the blood surrounding the internal balloon towards the aortic arch, upper and lower extremities and alternately sucking blood from the aortic arch, upper and lower extremities.

28. The method of claim 27, wherein a pressurization means coupled to the internal and external balloons is provided to pressurize the balloons.

29. The method of claim 28, wherein the pressurization means comprises a first lumen operatively coupled to the internal balloon and a second lumen operatively coupled to the external balloon, the first and second lumens being coupled to a external control unit.

30. The method of claim 27, further providing a second hollow catheter tube that extends the longitudinal length of the external balloon and is coupled to the external balloon.

31. The method of claim 30, wherein the second hollow catheter tube can be coupled to a pressure sensing device.

32. The method of claim 30, wherein the second hollow catheter tube can be used to inject substances into the human.

33. The method of claim 27, wherein the hollow catheter tube extends a length such that the catheter exits the human at the femoral artery.

34. The method of claim 27, wherein a perfusion eyelet having an open and a closed position is associated with the first hollow catheter tube.

35. The method of claim 34, wherein the perfusion eyelet is opened by pressurizing a circular balloon located circumferentially at the eyelet.

36. The method of claim 35, wherein a eyelet lumen is coupled to the circular balloon to independently control the pressurizing of the circular balloon.

37. The method of claim 27, wherein a gas is used to pressurize the internal and external balloons.

38. The method of claim 27, wherein the balloons and the hollow catheter tube of the device are fitted to the size of the patient.

* * * * *